United States Patent [19]

Pischinger et al.

[11] Patent Number: 5,005,402
[45] Date of Patent: Apr. 9, 1991

[54] MEASURING CELL FOR DETERMINATING THE ALCOHOL CONTENT AND/OR CALORIFIC VALUE OF FUELS

[75] Inventors: Franz Pischinger; Ernst Scheid; Ulrich Hilger; Gunter Schmitz, all of Aachen, Fed. Rep. of Germany

[73] Assignee: FEV Motorentechnik GmbH & Co. KB, Aachen, Fed. Rep. of Germany

[21] Appl. No.: 446,780

[22] Filed: Dec. 6, 1989

[30] Foreign Application Priority Data

Dec. 22, 1988 [DE] Fed. Rep. of Germany ....... 3843243

[51] Int. Cl.⁵ .................... G01N 27/22; F02D 41/04
[52] U.S. Cl. .................... 73/61.10 R; 123/1 A; 324/663
[58] Field of Search ............ 73/23, 117.3, 61.1 R; 123/1 A; 324/663

[56] References Cited

U.S. PATENT DOCUMENTS

| | | | |
|---|---|---|---|
| 4,594,968 | 6/1986 | Degobert et al. | 123/1 A |
| 4,905,649 | 3/1990 | Washino et al. | 73/117.3 X |
| 4,905,655 | 3/1990 | MaeKawa | 123/1 A X |

OTHER PUBLICATIONS

Proceedings of the Fourth International Symposium on Alcohol Fuels Technology, Sao Paulo, Brazil, Oct. 5, 1980, pp. 379–383.

Primary Examiner—Hezron E. Williams
Assistant Examiner—Joseph W. Roskos
Attorney, Agent, or Firm—Watson, Cole, Grindle & Watson

[57] ABSTRACT

A device for the determination of the alcohol content and/or the calorific value of fuels by measuring the characteristics of the fuel in a measurement cell in which a flow body that is at least partially wetted by the fuel is arranged. The accuracy and speed of this measurement is improved by providing a first electrode for the dielectric measurement of the fuel and a second electrode for the measurement of the conductivity of the fuel on the outside of the flow body. Preferably the first electrode for the measurement of the capacitance, its outer connection and the walls of the measurement cell form a mechanically rigid system. It can also be expedient to mount the measuring circuit for the measurement of at least the capacitance directly on the housing of the measurement cell.

11 Claims, 2 Drawing Sheets

FIG. 1

MEASURING CELL FOR DETERMINATING THE ALCOHOL CONTENT AND/OR CALORIFIC VALUE OF FUELS

The present application relates to commonly owned U.S. Pat. No. 4,945,863 and patent application Ser. No. 391,248, filed Aug. 9, 1987 and the concurrently filed and commonly owned patent application Ser. Nos. 446,726; 446,781; and 446,728, and 64,167, which are hereby incorporated by reference.

BACKGROUND OF THE INVENTION

1. Technical Field of the Invention

The invention relates to a device for the determination o the alcohol content and/or the calorific value of fuels by measuring the characteristics of the fuel in a measurement cell having a flow body that is at least partially wetted by the fuel arranged therein

2. Discussion of the Related Art

In light of diminishing fossil energy reserves of fuels obtained from crude oil and stricter environmental protection requirements, increasing amounts of methyl or ethyl alcohol are being added to these fuels. Thus, any arbitrary refueling should be possible both with pure fuels and mixed fuels. When the alcohol content is higher, it is necessary to know the blending ratio in order to obtain optimal performance from the fuel-burning engine and to enable a precise proportioning of fuel adjusted to the operating conditions. The continuous determination of the alcohol content in the fuel fed into the fuel-burning engine in operation presents special problems for automobile engines in which any possible blend may be present by arbitrary refueling with various types of fuel.

In the German patent application P38,10808.9, a device of the aforementioned kind is described in which the characteristics of the fuel are measured in a measurement cell and processed in a suitable circuit. This circuit in turn is connected to an injection computer whose results are evaluated in order to control a fuel proportioning device.

It has been demonstrated that in measuring devices of this kind, high measurement accuracy and fast availability of measured values is mandatory in order to adjust fuel proportioning to the rapidly changing operating conditions.

Accordingly, it is an object of the present invention to provide a device for the determination of the alcohol content and/or of the calorific value of fuels which enables the measured values to be supplied rapidly with high accuracy of measurement.

Other objects and advantages of present invention are apparent from the drawing and specification will follow.

SUMMARY OF THE INVENTION

The foregoing and additional objects are obtained by a device according to the present invention for determining the alcohol content and/or the calorific value of fuels of the kind described above. An internal flow body has on its outside a first electrode for the dielectric measurement of the fuel and a second electrode for the measurement of the conductivity of the fuel. Preferably the first electrode for the measurement of the capacitance, its outer connection and the walls of the measurement cell form a mechanically rigid system. Both in light of the attainable accuracy of the measurement and its analysis and also in light of the low cost of production and efficient utilization of space, at least the measuring circuit of the capacitance can be mounted directly on the housing of the measurement cell.

A preferred embodiment provides that the important centering of the internal body serving as the internal electrode for a defined capacitance is performed by means of a cage which is made of a non-conducting material and which at the same time can also serve as the mounting for the internal body.

To improve the measuring process and the computer analysis, the measurement cell can also have an additional sensor to measure the temperature of the fuel flowing through the measurement cell.

The internal flow body can be made of a glass fiber reinforced plastic such as polytetrafluoroethylene, i.e., PTFE. or also of a ceramic material on whose outside the electrodes are mounted. It can also be made of steel on which the electrodes are mounted so as to be insulated.

The area of the electrode specified for the dielectric measurement may be twice the electrode used for the measurement of conductivity, and the electrode specified for the measurement of conductivity can be arranged in the flow direction of the fuel at a distance from the electrode specified for the dielectric measurement.

DETAILED DESCRIPTION OF THE PREFERRED EMBODIMENTS

The present invention will now be described in great detail with reference to the accompanying drawings.

Figure 1:
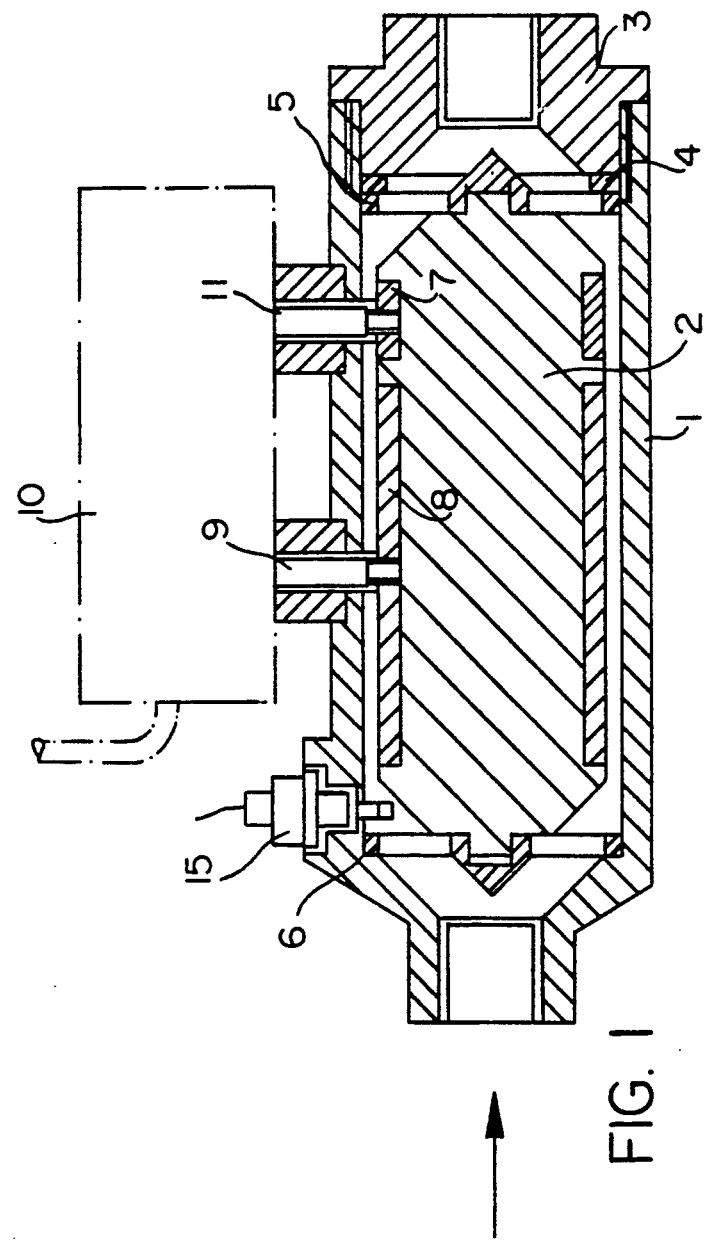
FIG. 1 is a longitudinal view of a simplified and primarily schematic drawing of the first embodiment of a measurement cell.

FIG. 1 shows a longitudinal view of a measurement cell which is suitable to determine the alcohol content and/or the calorific value of fuels by means of a capacitive dielectric measurement. The measurement cell has an electrically conductive housing 1 in which a primarily cylindrical flow body 2 is centered. A fixing of the flow body 2 is achieved by means of a lock plug 3 which exerts pressure on a mounting part 5 by means of an elastic contact disk 4, e.g., by means of a PTFE ring, and thus forces the flow body 2 against a holder 6 mounted in the housing 1. The lock plug 3 serves simultaneously to connect the fuel line to the cell.

Electrodes 8 and 7 are made of a electrically conductive material and are used for the dielectric or conductivity measurement and are located on the outside of the flow body 2, which can also be divided if desired. The size of the surface of the plate areas that are used for the capacitive dielectric measurement depends on the capacitance required at a minimum for the electronic measuring circuit, whereas a relatively small electrode surface suffices for the conductivity measurement. For the measurement of the dielectric constants of the fuel flowing between the outer electrode formed by the housing 1 of the measurement cell and the opposing electrode 8 located on the flow body, it is especially advantageous if an electric connection 9 of the internal electrode with the electronic measuring circuit has a capacitance that is constant under all operating conditions. This is achieved by designing the electric connection between the electrode 8 and the measurement circuit 10 to be rigid. To this end, for example, a PTFE-jacketed threaded pin is screwed to the electrode 8 through the housing passage, wherein a cutting ring-pipe screw coupling can be used to position and seal the electric connection in the housing 1. The electric connection 11 of the electrode 7 for the conductivity measurement can also be conducted by means of a flexible guide in place of the rigid connection that is shown. The measuring circuit to determine the capacitance is mounted directly on the housing 1 of the measurement cell in an advantageous manner to avoid disturbing influences. For example, measuring circuit 10 is fastened directly on the measurement electrode connections 9 and 10.

Alcohol resistant material such as high-alloyed corrosion resistant steels are used for the housing 1 and for the flow body 2. The flow body 2 can also be made of PTFE plastic or ceramic material. In this case the internal electrodes 7 and 8 are mounted, e.g., in the shape of steel rings, on the outside of the flow body 2. The flow body 2 can also be made of steel in this case, the electrodes 7 and 8 are mounted on the flow body 2 with appropriate insulation.

As FIG. 1 shows, a sensor 15 is provided to measure the temperature of the fuel flowing through the measurement cell in order to be able to eliminate the influence of the temperature during the analysis.

Figure 3:
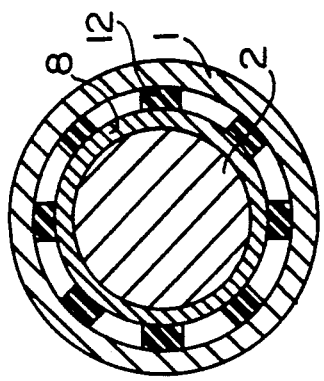
FIG. 3 is a cross sectional view of the embodiment shown in FIG. 2.
Figure 2:
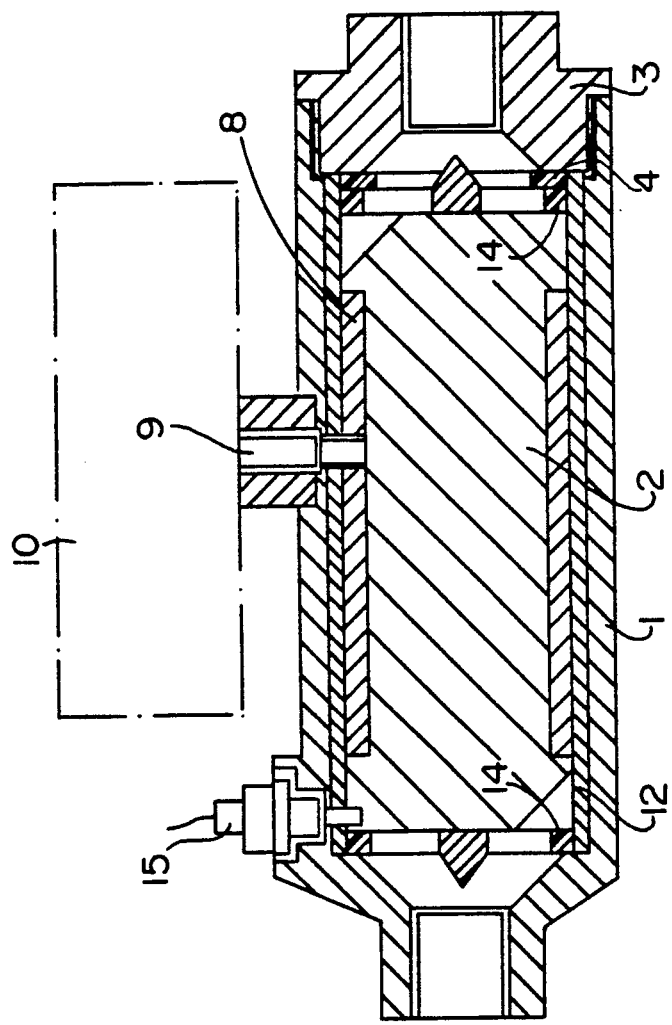
FIG. 2 is a view similar to that of FIG. 1 of another embodiment.
Figure 4:
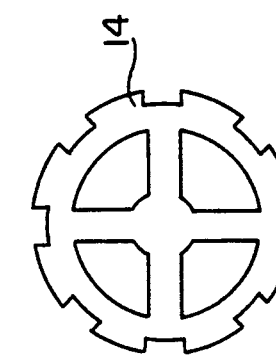
FIG. 4 shows the a detailed view of the disc of the FIG. 2 embodiment.

Another embodiment is shown in FIGS. 2-4. The flow body 2 is enclosed by a cage 12 made of an electrically non-conducting material, and connected to the internal wall of the housing 1. Thus, a constant, precisely defined distance is maintained over the entire length between the internal electrode 8 of the flow body 2 and the outer electrode formed by the housing 1 so that the production variations that are especially critical for the capacitance measurement are minimized. The cage 12 comprises at least three gate elements. A disk 14 supports the ends of cage 12 and the internal flow body 2. To obtain especially small production variations, the gate elements may be plastic elements pre-fabricated with high accuracy.

Other modifications and improvements will be apparent to one skilled in the art without departing from the spirit and scope of the present invention as defined in the following claims.

We claim:

1. A measurement cell for determining the alcohol content and calorific value of a fuel, the cell including a housing having inner walls defining a cavity for a flow of a fuel in a particular direction, the measurement cell comprising:
   a symmetrical flow body located within the cavity, said flow body and the inner walls of the housing being parallel and thereby defining a passageway for the flow of fuel through the cavity in the particular direction and around the flow body, whereby the flow body is wetted by the fuel;
   a first electrode located on the outside of said flow body; and
   an electronic measuring circuit connected to said first electrode to measure the capacitive dielectric of the fuel.

2. The measurement cell according to claim 1, further comprising a second electrode located on the outside of said flow body and connected to said electronic measuring circuit to measure the conductivity of the fuel.

3. The measuring cell according to claim 2, wherein the area of said first electrode for the dielectric measurement is at least twice the area of said second electrode for the measurement of conductivity.

4. The measuring cell according to claim 2, where said first electrode is arranged in direction of a flow of the fuel at a distance from said second electrode.

5. The measurement cell according to claim 1, further comprising an electric connection rigidly extending between said first electrode, through a wall of the cell and to said measuring circuit.

6. The measuring cell according to claim 1, wherein said measuring circuit is mounted on the housing of the measurement cell.

7. The measuring cell according to claim 1, further comprising a cage made of non-conducting material connected to the flow body and to the interior of the housing to mount and center said flow body, whereby the capacitance of the fuel is more accurately determined.

8. The measuring cell according to claim 1, further comprising a sensor to measure the temperature of the fuel flowing through the measurement cell.

9. The measuring cell according to claim 1, wherein said flow body is made of a glass fiber reinforced polytetrafluoroethylane plastic.

10. The measuring cell according to claim 1, wherein said flow body is made of a ceramic material.

11. The measuring cell according to claim 1, wherein said flow body is made of steel and said first electrode is insulated.

* * * * *